United States Patent [19]

Rubio et al.

[11] Patent Number: 5,424,297
[45] Date of Patent: Jun. 13, 1995

[54] ADENOSINE DEXTRAN CONJUGATES

[75] Inventors: Rafael Rubio; Eduardo Balcells, both of Charlottesville, Va.; Jorge Suarez, Neizahualcoyoil, Mexico

[73] Assignee: University of Virginia Alumni Patents Foundation, Charlottesville, Va.

[21] Appl. No.: 214,680

[22] Filed: Mar. 21, 1994

Related U.S. Application Data

[63] Continuation of Ser. No. 874,044, Apr. 27, 1992, abandoned.

[51] Int. Cl.$^6$ .................... A61K 31/715; A61K 31/52; C07H 19/167
[52] U.S. Cl. ...................... 514/46; 514/814; 536/26.13; 536/112; 544/272; 544/273
[58] Field of Search ............... 514/46, 814; 536/26.13, 536/112; 544/272, 273

[56] References Cited

PUBLICATIONS

Sigma Chemcial Catalog, 1990, Sigma Chemical Company, Inc., St. Louis, Mo.
Votruba et al. Collection Czechoslovak Chem. Commun. vol. 48, pp. 2549–2557, 1983.
Balcells et al. European Journal of Pharmacology, vol. 210, pp. 1–9, 1992.
Lippman, Richard D. J. Biochem. Biophys. Methods, vol. 6, pp. 81–87, 1982.
Clemo, Henry F. and Luiz Belardinelli. "Effect of Adenosine on Atrioventricular Conduction. II: Modulation of Atrioventricular Node Transmission by Adenosine in Hypoxic Isolated Guinea Pig Hearts", *Circulation Research*, vol. 59. No. 4, Oct. 1986, pp. 437–446.
Nees, S. et al. "The Coronary Endothelium: a Highly Active Metabolic Barrier for Adenosine", *Basic Research in Cardiology*, vol. 80, No. 5 (1985), pp. 314, 517–529.
Spielman, William S. "Antagonistic Effect of Theophylline on the Adenosine-Induced Derease in Renin Release", pp. F246–F251, 1984.
Schrader, Jürgen et al. "Evidence for a cell Surface Adenosine Receptor on Coronary Myocytes and Atrial Muscle Cells", *Pflugers Arch. 369: European Journal of Physiology*, (1977), pp. 251–257.
Armstrong, Kenneth J. et al. "Dextran-Linked Insulin: A soluble High Molecular Weight Derivative with Biological Activity In Vivo and In Vitro", *Biochemical and Biophysical Research Communications*, vol. 47, No. 2, (1972), pp. 354–360.
Olsson, Ray A. et al. "Evidence for an Adenosine Receptor on the Surface of Dog Coronary Myocytes", *Circulation Research*, vol. 39, No. 1, Jul. 1976. pp. 94—98.
Balcells, Eduardo et al. "Functional Role of Intravascular Coronary Endothelial Adenosine Receptors", *European Journal of Pharmacology*, 210 (1992), pp. 1–9.
Balcells, Eduardo et al. "Functional Role of Intravascular Coronary Endothelial Adenosine Receptors", *European Journal of Pharmacology*, 210 (1991), pp. 1–9.
Rubio, R. et al. "Adenosine Receptor Agonists and Antagonists II (8118–8122)", *FASEB J.*, vol. 5, No. 6: A1769, Apr. 25, 1991, No. 8118.
Balcells, E. et al., *Abstract of the 63rd Scientific Sessions*, vol. 82:III-149, Nov. 15, 1990, No. 0590.
Bruns, R., *Biochemical Pharmacology*, vol. 30, pp. 325, Pergamon Press Ltd. 1981, "Adenosine Antagonism by Purines, Pteridines and Benzopteridines in Human Fibroblasts".
Jacobson, K. et al., *Biochemical Pharmacology*, vol. 36, No. 10, pp. 1697, 1987 "Molecular Probes for Extracellular Adenosine Receptors".

(List continued on next page.)

Primary Examiner—Douglas W. Robinson
Assistant Examiner—Gary L. Kunz
Attorney, Agent, or Firm—Oblon, Spivak, McClelland, Maier & Neustadt

[57] ABSTRACT

Covalent conjugates of water soluble dextrans and adenosine agonists or antagonists wherein the dextran is coupled through the C6 or C8 positions of the purine ring. These compounds activate or block adenosine $A_1$ or $A_2$ receptors are useful in treating hypertension.

16 Claims, 10 Drawing Sheets

OTHER PUBLICATIONS

Jacobson, K. et al., *J. Med. Chem.*, 32:1043, 1989, "Electrophilic Derivatives of Purines as Irreversible Inhibitors of $A_1$ Adenosine Receptors".

Daly, J. et al., *Biochemical Pharmacology*, vol. 35, No. 35, pp. 2467, 1986, "Structure-Activity Relationships for $N^o$-Substituted Adenosines at a Brain $A_1$-Adenosine Receptor with a Comparison to an $A_2$-Adenosine Receptor Regulating Coronary Blood Flow".

Daly, J. et al., *J. Med. Chem.*, 28:487, 1984, "1,3-Dialkyl-8-(p-p-sulfophenyl)xanthines: Potent Water-Soluble Antagonists for $A_1$-and $A_2$-Adenosine Receptors".

Cristalli, G. et al., *J. Med. Chem.*, 31:1179, 1988, "Adenosine Receptor Agonists: Synthesis and Biological Evaluation of 1-Deaza Analogues of Adenosine Derivatives".

Bridges et al., *J. Med. Chem.*, 31:1282-1285, 1988, "$N^6$-[2-(3,5-Dimethoxyphenyl)-2-(2-methylphenyl)--ethyl]adenosine and Its Uronamide Derivatives, Novel Adenosine Agonists with both High Affinity and High Selectivity for the Adenosine $A_2$ Receptor".

Jacobson, K. et al., *fEBS Letters*, 225:97, 1987, "Adenosine Analogs with Covalently Attached Lipids Have Enhanced Potency at $A_1$-Adenosine Receptors".

Stiles, G. et al., *Molecular Pharmacology*, 82:184, 1987, "A New High Affinity, Iodinated Adenosine Receptor Antagonist as a Radioligand/Photoaffinity Crosslinking Probe".

Jacobson, K. et al., *Molecular Pharmacology*, 29:126, 1985, "A Functionalized Congener Approach to Adenosine Receptor Antagonists: Amino Acid Conjugates of 1,3-Dipropylxanthine".

Olafsson, B. et al., *Laboratory Investigation*, vol. 76, No. 5, Nov. 1987, "Reduction of reperfusion injury in the canine preparation by intracoronary adenosine: importance of the endothelium and the no-reflow phenomenon".

Babbit, D. et al., *Circulation;* 80:1388, 1989, "Intracoronary Adenosine Administered After Reperfusion Limits Vascular Injury After Prolonged Ischemia in the Canine Model".

Liu G. et al., *Circulation;* 84:350, 1991, "Protection Against Infarction Afforded by Preconditioning is Mediated by $A_1$ Adenosine Receptors in Rabbit Heart".

FIG. 9A   FIG. 9B   FIG. 9C
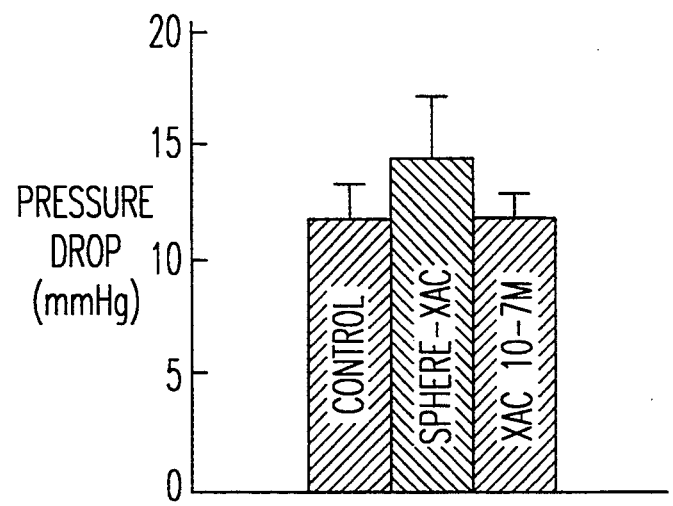
FIG. 9D
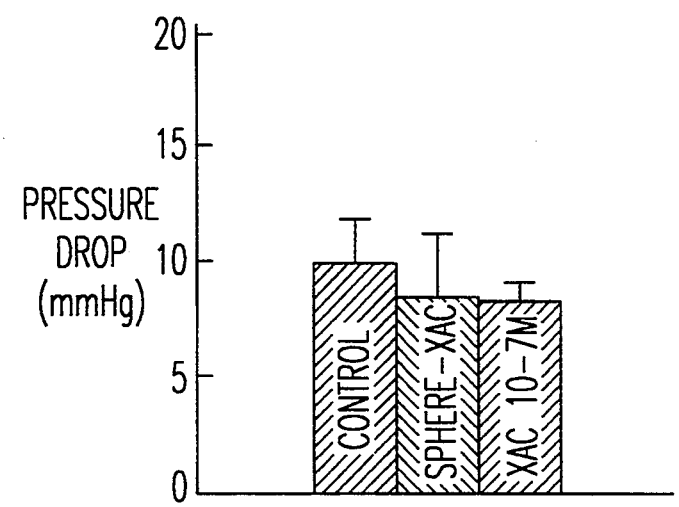
FIG. 9E

ADENOSINE DEXTRAN CONJUGATES

This application is a continuation of application Ser. No. 07/874,044, filed on Apr. 27, 1992, now abandoned.

BACKGROUND OF THE INVENTION

1. Field of the Invention

The present invention is directed to adenosine agonist and antagonist compounds covalently coupled to medium molecular weight and high molecular weight dextrans and microbeads. These adenosine agonist and antagonist complexes alone or in combination are able to selectively activate intravascular endothelial adenosine receptors as well as extravascular adenosine receptors.

2. Discussion of the Background

Adenosine is a low molecular weight (Mw=267) naturally occurring nucleoside having several receptor-mediated effects in mammals with potential therapeutic use. These effects of adenosine can be blocked at the receptor level by theophylline and other methylxanthines. The effects of intravascular administration of adenosine include: coronary and general vascular dilation, inhibition of the release of renin and catecholamine, auricular-ventricular blockade and spontaneous ventricular tachycardial depression and reduction of myocardial perfusion injury. Thus, adenosine can potentially be a coronary vasodilator, an anti-hypertensive agent (by causing general vascular dilation and inhibition of the release of renin and catecholamines) and an antiarrhythmic agent and a protective agent against myocardial infarction.

However, when adenosine is given intravascularly, it distributes itself throughout the entire extracellular (intravascular plus intrastitial) compartment, thereby being able to affect all cells containing adenosine receptors. Additionally, adenosine is rapidly taken up by all cells and inactivated by metabolizing enzymes. These two properties limit the therapeutic use of this nucleoside. Due to lack of compartmentalization, adenosine cannot act solely on specific target cells, but affects all cells and thereby loses specificity. Further, adenosine is rapidly metabolized so that its effects are very transitory and have no stability.

The cardiovascular actions of adenosine have been extensively studied and include coronary vasodilation, a negative chronotropic/dromotropic effect, an anti-adrenergic response and cardiac protection against infarction (Olafsson et al, *Circulation*, 76(5):1135–1145 (1987); Babbitt et al, *Circulation*, 80:1388–1399 (1989); Liu et al, *Circulation*, 84:350–356 (1991)). While it is now known that most of these actions are mediated via membrane bound receptors, the precise mechanisms by which adenosine exerts its cardiovascular effects have yet to be defined. Difficulties arise secondary to the numerous influences involved with the formation and metabolism of adenosine. With the myocardium, adenosine can be produced and metabolized by both the endothelium and cardiomyocytes, and is therefore subject to the influence of both cell types. The relative contribution of these two cell types to the extracellular level of adenosine is dependent on several physiological factors and is still an area of controversy. There is also uncertainty as to the actual site of action of adenosine and whether or not some of its vascular effects are in part mediated via the vascular endothelium.

Endothelial dependent vascular relaxation is a well studied phenomena and has been documented for several substances including acetylcholine, ATP, ADP and substance P. For a review see Furchgott, *Circ. Res.*, 53:557–73, 1983 and Luscher et al, *CRC*, Boca Raton, pp. 1–87, 1990. However, it has been difficult to establish the role of the vascular endothelium with respect to adenosine mediated vascular relaxation. For instance, studies on isolated arterial segments have shown a reduction in the vasodilatory effects of adenosine in endothelial denuded arterial segments. See Frank, G. W. and Bevan, J. A., *Regulatory Function of Adenosine*, Berne, R. M., Rall, T. W., Rubio, R. (eds), Martinus Nijhoff, Hague Boston London, p. 511 (1983); Haendrick, J., Berne, R. M., Am. J. Physiol., 259:H62–H67 (1990); Kennedy, C., Burnstock, G., *Blood Vessels*, 22:145–155 (1985); Moritoki, H., *Role of Adenosine and Adenine Nucleotides in the Biological System*, Imai S., Nakazawa, M. (eds), Elseveir, Amsterdam New York Oxford, pp. 217–224 (1991); Rubanyi, G. Vanhoutte, P. M., *J. Cardiovasc. Pharmacol.*, 7:139–144 (1985). At the same time, adenosine vasodilatory effects have been reported to be independent of the vascular endothelium. See Cassis, L. A., Loeb, A. L., Peach, M. J., *Topics and Perspectives in Adenosine Research*, Gerlach, E., Becker, B. F. (eds), Springer, Berlin Heidelberg New York, pp. 486–496 (1987); Luscher, T. F., Vanhoutte, P.M., *CRC*, Boca Raton, pp. 1–87 (1990); Mathieson, J. I., Burnstock, G., *Europ. J. Pharmacol.*, 118:221–229 (1985); Pearson, J. D., Gordon, J. L., *Nature*, 181:384–186 (1979). In some intact vascular beds, the endothelium may be necessary for the maximum vasodilatory response to adenosine. Nonetheless, it is not possible to assess the relative contribution of the vascular endothelium using conventional methods of comparing blood vessel responses both with and without the endothelium. This is because the vascular endothelium of intact vascular beds cannot be denuded without altering organ function. Moreover, the relative importance of the endothelium becomes evident if one considers that adenosine remains confined to the intravascular compartment during its intracoronary infusion, in up to micromolar concentrations, secondary to the impermeable metabolic barrier imposed by the endothelium (see Nees, S., Herzog, V., Becker, B. F., Bock, M., Des Rosiers, C., Gerlach, E., *Basic Res. Cardiol.*, 80:515–529 (1985); Nees, S., Herzog, V., Becker, B. F., Bock, M., Des Rosiers, C., Gerlach, E., *Adenosine: Receptors and Modulation of Cell Function*, Stefanovich, V., Rudolph, K., Schubert, P. (eds), IRI, Oxford, pp. 419–436 (1985); Nees, S., Gerlach, E., *Regulatory Function of Adenosine*, Berne, R. M., Rall, T. W., Rubio, R. (eds), Martinus Nijhoff, Hague Boston London, pp. 347–360 (1983)) and yet the vasodilatory and negative dromotropic effects of adenosine are observable at these concentrations (Nees, S., Gerlach, E., ibid.).

The pharmacokinetics of macromolecular adenosine analogs are similar to their low molecular weight counterparts during intracoronary infusion. Nees et al have studied the metabolic effects of perfusing isolated guinea-pig hearts with polyadenylic acid (poly-A; molecular weight: 100,000). See Nees, S., Herzog, V., Becker, B. F., Bock, M., Des Rosiers,, C., Gerlach, E., *Basic Res. Cardiol.*, 80:515–529 (1985). Olsson et al covalently bonded adenosine and theophylline to oxidized stachyose. Anesthetized dogs were then administered these compounds by intracoronary infusion to study dose-dependent coronary vasodilation. See Olsson, R. A., Davis, C. J., Khouri, E. M., Patterson, R. E., *Cir. Res.*, 39:93-98 (1976). Schrader et al covalently coupled adenosine monophosphate (AMP) to the enzyme carbonic anhydrase to produce a conjugate having a mean molecular weight of about 30,000. When infused into the coronary arteries of isolated guinea-pig hearts, the conjugate induced vasodilation which was similar in magnitude and time course to the vasodilation elicited by free AMP or adenosine. See Schrader, J., Nees, S., Gerlach, E., *Pfluger Arch.*, 369:251-257 (1977). Intracoronary infusion of adenosine deaminase, which deaminates adenosine to inosine, alters cardiovascular function and yet this enzyme remains largely intravascularly confined. Clemo, H. F., Belardinelli, L., *Cir. Res.*, 59:437-446 (1986).

Although Schrader et al, Nees et al and Olsson et al couple adenosine to larger molecules, these derivatives are not large enough to completely prevent the passage of the derivatives through the endothelium and outside of the vascular compartment. Selective activation of intravascular adenosine receptors is not possible with these relatively low molecular weight adenosine derivatives.

There is a continuing need for adenosine agonist and antagonist compounds which are useful in studying the functional significance of intravascular, endogenous and exogenous coronary adenosine. Further, adenosine compounds which selectively activate intravascular or interstitial adenosine receptors or which block these receptors are useful pharmaceutical agents in eliciting specific cardiovascular effects in mammals.

SUMMARY OF THE INVENTION

Accordingly, one object of the present invention is to provide adenosine agonist and antagonist compounds which are useful in studying cardiovascular adenosine receptors.

Another object of the invention is to provide adenosine agonist and antagonist pharmaceutical compounds which selectively bind to intravascular adenosine receptors.

A further object is to provide adenosine agonist and antagonist compounds which alone or in combination can be tailored to elicit a desired specific cardiovascular response.

These and other objects which will become apparent from the following specification have been achieved by the present adenosine agonist and antagonist compounds which are covalently coupled to medium molecular weight and high molecular weight dextrans or microbeads. When administered intravascularly, the medium molecular weight compounds equilibrate between the extracellular and the intravascular compartments. In contrast, the high molecular weight dextran compounds and compounds coupled to microbeads remain exclusively in the intravascular compartment. When a combination of high molecular weight dextran-adenosine antagonist and medium molecular weight dextran-adenosine agonist are administered intravascularly, the agonist will act solely on extravascular receptors because the intravascular effects are prevented by the high molecular weight dextran-antagonist. These selective distributions allow one to control the cardiovascular response to administration of the adenosine agonist and antagonist by adjusting the molecular weight of the coupled compounds.

BRIEF DESCRIPTION OF THE DRAWINGS

FIGS. 6(A-14 C) show pressure readings from individual experiments indicating a drop in perfusion pressure A: control during K-H only perfusion. B,C: bolus given after 5 minute of infusion with SPH-XAC and with XAC $10^{-7}$M, respectively. FIGS. 6(D-E) show compiled data for adenosine bolus experiments. D: control A (n=22) during K-H only perfusion, control B (n=7) during control microbead infusion, then during SPH-XAC (n=11), XAC $10^{-5}$M (n=6) and XAC $10^{-7}$M (n=6) infusion. E: effect of decreasing SPH-XAC concentration from 6.0 to 0,006 mg/ml (n=3);

FIG. 7 shows the time progression of Mobitz type II nodal heart block during 10 $\mu$l bolus injections of adenosine ($10^{-3}$M) at a stimulation frequency of 3.5 Hz.

FIG. 8 shows the effect of hypoxia (95% $N_2$+5% $CO_2$) on the A-V interval and recovery.

FIG. 9 shows the effect of hypoxia on coronary pressure. FIGS. 9(A-C): individual pressure readings during a 2.0 minute period of hypoxia (95% $N_2$+5% $O_2$). A: control, K-H perfusion only. B: 6.0 mg/ml SPH-XAC infusion. C: $10^{-7}$M free XAC infusion. FIG. 9(D): drop in mean coronary pressure during hypoxia (95% $N_2$+5% $O_2$) for control (n=10), XAC $10^{-7}$M (n=4), SPH-XAC 6.0 mg/ml (n=8).FIG. 9(E): drop in mean coronary pressure during hypoxia (75% $N_2$+20% $O_2$+5% $CO_2$) for control (n=5), XAC $10^{-7}$M (n=4), SPH-XAC 6.0 mg/ml (n=4);

DETAILED DESCRIPTION OF THE PREFERRED EMBODIMENTS

Figure 1A:
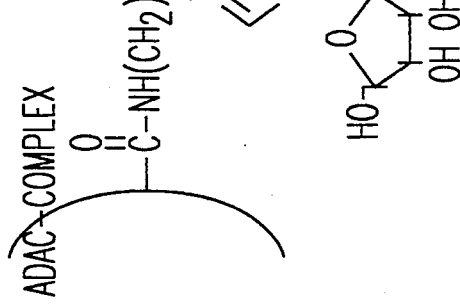
FIG. 1 shows the chemical structures of preferred adenosine derivatives of the present invention covalently bonded to a polymer microbead.
Figure 1B:
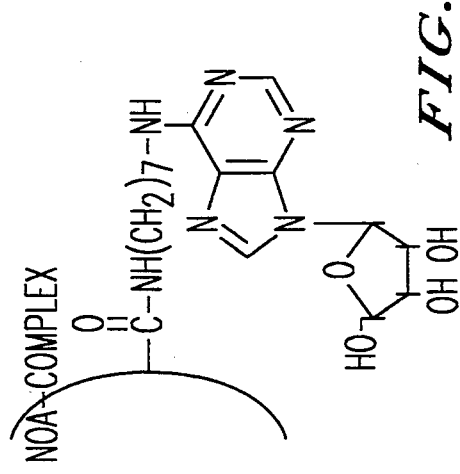
Figure 1C:
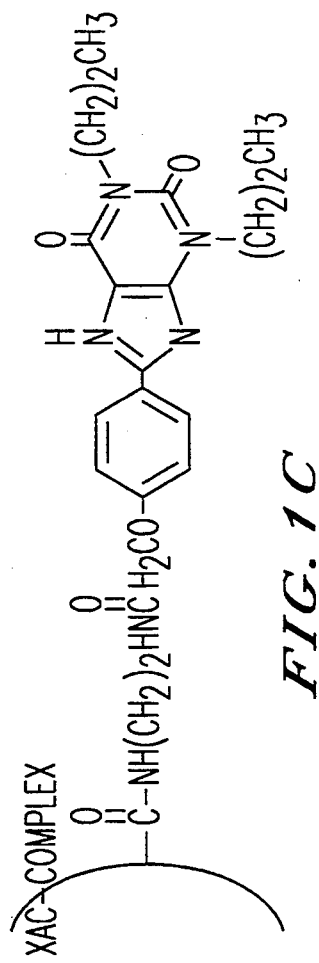

In the present invention, the nucleoside adenosine, an adenosine agonist or an adenosine antagonist are covalently coupled to a microbead or to a dextran. Since these compounds are larger than adenosine, they are not accessible to intracellular adenosine metabolizing enzymes and are, therefore, more stable, remain in the circulation and act for longer periods of time than adenosine. By manipulating the molecular size of the adenosine derivative, one gains specificity by regulating the distribution of the adenosine compound between the intravascular and extravascular/interstitial compartments, thereby preferentially affecting a specific adenosine receptor population.

The high molecular weight and medium molecular weight adenosine agonists of the present invention are substitutes for adenosine in pharmaceutical and research applications. The agonists of the present invention interact with the adenosine $A_1$ and $A_2$ receptors producing physiological effects similar to adenosine itself. However, the agonists of the present invention have significantly prolonged effects since these higher molecular weight agonists are not enzymatically degraded by intracellular adenosine metabolizing enzymes.

The high molecular weight and medium molecular weight antagonists of the present invention are useful in pharmaceutical applications requiring blockade of adenosine $A_1$ receptors, for example hypoxia-related conditions. Hypoxia (low blood oxygen partial pressure) frequently occurs in coronary artery disease and pulmonary disease. Hypoxia results in the production of endogenous adenosine which increases the A-V delay. Blockade of the endothelial $A_1$ adenosine receptors with the antagonists of the present invention significantly shortens the A-V interval, increasing heart rate thereby providing increased oxygen to the patient.

The effects of a high molecular weight adenosine agonist or antagonist compound result only from endothelial adenosine receptor activation or blockade since the high molecular weight adenosine agonist or antagonist compound is retained within the intravascular compartment. Conversely, a medium molecular weight adenosine agonist or antagonist compound can act on endothelial as well as extravascular cells, since the medium molecular weight compounds can pass through the vascular wall.

As used herein, the term "adenosine derivative" refers to adenosine, all adenosine agonists and adenosine antagonists which may be covalently bonded or coupled to a polymer microbead or to a dextran having a molecular weight of about 1,000–5,000,000 Daltons. The term "high molecular weight" refers to an adenosine derivative covalently bonded to a polymer microbead or to an adenosine derivative covalently bonded to a dextran having a molecular weight of about 1,000,000–5,000,000 Daltons (1,000–5,000 kD). The term "medium molecular weight" refers to an adenosine derivative covalently bonded to a dextran having a molecular weight in the range of about 1,000 up to 1,000,000 Daltons (1–999 kD). The terms "medium molecular weight" and "high molecular weight" are used herein to qualitatively describe the vascular distribution properties of adenosine derivatives coupled to microbeads or dextrans. Obviously, adenosine derivatives coupled to dextrans having molecular weight just below 1,000,000 Daltons (1,000 kD) will exhibit properties similar to the high molecular weight coupled compounds.

A diversity of polymer microbeads made by polymerization or copolymerization of a diversity of monomers including, but not limited to styrene, divinylbenzene, maleic anhydride, acrylamide, etc., are commercially available having a particle size range from about 0.01 microns to about 100 microns average diameter (Bangs, Seradyn, Inc.). These microbeads are manufactured using known methods and are characterized by a diversity of surface functional groups such as: carboxylic (—COOH), amidic (—CO—$NH_2$), aldehydic (—CHO), aromatic amine (—$C_6H_5$—$NH_2$), hydrazidic (—NH—$NH_2$) and hydroxylic (—OH) groups. These surface functional groups are used to covalently bond the adenosine derivative to the microbead. The chemical reactions which are used to form covalent bonds between the surface functional groups of the microbead and the adenosine derivative are well known in the art. For example, carboxylate modified microbeads may be covalently bonded to an adenosine derivative through amide or ester linkages. Hydroxyl surface groups on the microbead can be reacted using appropriate chemical reactions to form ether, ester or carbamate linkages. Aromatic amine surface functional groups can be used to form amide, carbamate or urethane linkages. The diversity of surface functional groups permits the selection of known chemistries in coupling the adenosine derivatives to the microbeads. Preferred microbeads are carboxylate modified polymer microbeads having an average diameter greater than 0.015 microns.

Particularly preferred carboxylate modified polymer microbeads are commercially available having a surface charge density ranging from about 0.1 to about 0.3 meq/g and average diameters of about 0.05–1.0 microns (Bangs; Seradyn Inc.). Preferred carboxylate modified microbeads are produced by copolymerizing a vinyl carboxylic acid or anhydride with styrene to produce a carboxylate modified polystyrene latex microbead.

An adenosine derivative may be covalently coupled to microbeads or derivatized, i.e., carboxylate modified, microbeads by any known coupling reaction. The method of coupling the adenosine derivative to the microbead is not critical, so long as the covalently coupled product retains activity and is stable under physiological conditions. That is, the adenosine derivative can be covalently bonded to the microbead by any known method which produces a product in which the adenosine derivative does not dissociate or hydrolyze from the microbead during or after intravascular infusion. Preferably, the adenosine derivative is coupled to a carboxylate modified microbead, since these derivatized microbeads are readily available.

In a preferred embodiment, using carboxylate modified microbeads, the microbeads are first contacted with an anionic/cationic exchange resin to fully remove all water-soluble ions, including polymeric materials, leaving only the surface carboxylate groups on the microbeads. Generally, the carboxylate modified microbeads are simply stirred in deionized water with an excess of the ion exchange resin. The exchange resin: microbead w/w ratio should be about 2:1 to about 5:1. After removal of the ion exchange resin, the pH of the filtered colloidal mixture can be titrated with sodium hydroxide to a pH of about 6.0-8.0, preferably about 6.5-7.5. The microbeads are then activated by reaction with 1-(3-dimethyl aminopropyl)-3-ethyl carbodiimide at a molar ratio of about 5:1 in combination with N-hydroxysuccinimide at a molar ratio of about 4:1. The N-hydroxysuccinimide stabilizes the acylurea activated intermediate. The activated microbead mixture which is produced is then ready for direct coupling to an adenosine derivative.

Preferred adenosine agonists which may be covalently bonded to carboxylate modified microbeads or to dextrans include all adenosine agonists which have a free primary or secondary amino group available for reaction with a free carboxyl group or reactive derivative thereof (anhydride, acid halide) or with reactive isothiocyanate, N-hydroxysuccinimide ester, maleimide, or sulfonyl chloride groups. The agonists may be bonded directly to an available carboxyl group on the polymer microbead or, optionally, may be bonded to a free carboxyl group of a spacer molecule, where the spacer molecule is itself bound to the microbead.

Suitable adenosine agonists include $N^6$-phenyladenosines, $N^6$—$C_{5-8}$cycloalkyl adenosines $N^6$—$C_{1-6}$alkyladenosine-5'-uronamides, 2-halo-adenosines, as well as the corresponding deazaadenosine compounds, for example $N^6$-1-methyl-2-phenethyl-1-deazaadenosine, $N^6$-cyclopentyl-1-deazaadenosine, $N^6$-cyclohexyl-1-deazaadenosine. Synthetic methods for preparing suitable adenosine agonists are well known in the art. See Jacobson et al, Biochem. Pharm., 36(10):1697–1707 (1987); Daly et al, Biochem. Pharm., 35(15):2467–2481 (1986); Cristalli et al, J. Med. Chem., 31:1179 (1988); Bridges et al, J. Med. Chem., 31:1282–1285 (1988); Jacobson et al, FEBS Letters, 225:97–102 (1987). Preferred agonists have the structure shown below:

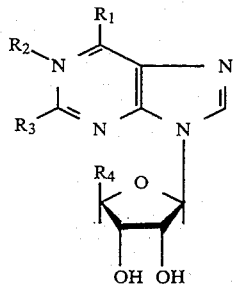

where $R_1$ is a substituent which contains a free amino group. Examples of substituent $R_1$ include $NH_2$; $NH_2$—$(CH_2)_n NH$—, where $n=1-10$; $NH_2$—$C_{6-20}$ arylene-; $NH_2$—$C_{5-6}$ cycloalkylene- and —NH—$C_6H_5$—$CH_2CONH$—$C_6H_5$—$CH_2CONH$—$(CH_2)_n$—$NH_2$. Preferably, $R_1$ is amino. In the formula shown above, $R_2$ and $R_3$ may be any substituent which allows the coupled agonist to retain activity. Suitable substituents $R_2$ and $R_3$ include hydrogen, halogen, oxo (=O, $R_3$ only) $C_{1-6}$ alkyl, —NH—$(CH_2)_o$—$C_6H_5$—$(CH_2)_p$—COOH, where o and p are 1-4, etc. Substituent $R_4$ is generally hydroxymethyl ($CH_2OH$) but also includes $C_{1-6}$ alkylcarboxamido ($C_{1-6}$alkyl-NHCO—) and $C_{3-6}$ cycloalkylcarboxamido ($C_{3-6}$cycloalkyl-NHCO—) groups.

Specific examples of suitable adenosine agonists include $N^6$-octylaminoadenosine, 2-[4-(2-carboxyethyl)-phenethylamino]-5'-N-ethylcarboxamidoadenosine; adenosine; $N^6$-[[[(2-aminoethyl)amino]carbonyl]methyl]phenyl]adenosine (adenosine amine cogener, ADAC); $N^6$-benzyladenosine; CGS-21680; 2-chloroadenosine; 2-chloro-$N^6$-cyclopentyladenosine; CV-1808; $N^6$-cyclohexyladenosine (CHA); $N^6$-cyclopentyladenosine (CPA); 5'-(N-cyclopropyl)-carboxamidoadenosine; 1-deaza-2-chloro-$N^6$-cyclopentyladenosine; DPMA (PD-125944); 5'-N-ethylcarboxamidoadenosine (NECA); $N^6$-methyladenosine; $\alpha,\beta$-methylene ATP lithium salt; 5'-N-methylcarboxamidoadenosine; 1-methylisoguanosine; 2-methylthio-ATP; $N^6$-phenyladenosine; $N^6$-phenylethyladenosine; 1-phenyl-2-isopropyladenosine (PIA), RR(−)-; PIA, S(+)-; $N^6$-hydroxylphenylisopropyladenosine (HPIA); and $N^6$-azidophenylethyladenosine (AZPNEA).

When $R_1$ is amino, a spacer molecule is generally used to bind the adenosine agonist to the microbead. Suitable spacer molecules include, for example, $\omega$-aminocarboxylic acids in which the free $\omega$-amino group is available to form an amide bond with the carboxylate group on the microbead and the carboxylic acid group of the spacer is available to form an amide bond with the amino group on the adenosine agonist ($R_1$). These spacer groups, therefore, form stable diamide linkages covalently linking the adenosine agonist to the carboxylate modified microbead. Preferred $\omega$-aminocarboxylic acids are $C_{3-12}$ alkylene, $C_{6-12}$ arylene and $C_{7-15}$ aralkylene $\omega$-aminocarboxylic acids.

Spacer molecules suitable for reaction with microbeads having surface amidic, aldehydic, aromatic amine, hydrazidic or hydroxyl groups will contain a functional group suitable for reaction with the amino group of the adenosine derivative, such as a carboxylic acid, acid anhydride or acid halide group, as well as a functional group suitable for reaction with the surface functional group on the microbead. Functional groups on the spacer molecule suitable for reaction with amide, aldehyde, aromatic amine, hydrazide or hydroxyl groups on the microbead include carboxylic acid, anhydride and acid halide groups. Amine and hydroxyl groups on the spacer molecule are suitable for reaction with surface carboxylic acid or aldehyde groups. Hydroxyl groups and amine groups may be protected if necessary using known acid or base stable protecting groups. Synthetic procedures for derivatizing carboxylate modified polymer beads to form surface amidic, haldehydic, amine, hydrazidic and hydroxyl groups, as well as synthetic procedures to covalently couple spacer molecules to these polymer beads are well known and any of the synthetic procedures may be used to couple the adenosine derivative to the microbead in the present invention. See, for example, Uniform Latex Particles, Seradyne, Inc., Indianapolis, Ind. (1987) and the references cited therein and Jacobson et al, J. Med. Chem., 32:1043–1051 (1989).

Adenosine antagonists which can be coupled to microbeads or dextrans to prepare the compounds of the present invention in a similar manner include 9-substituted adenosines, benzo[g]pteridines, xanthines, methylxanthines, such as aminophylline, etc. Other adenosine antagonists suitable for use in the present invention include 8-phenyltheophilines, 1,3-di-$C^{1-6}$-alkyl-8-phenylxanthines, 1,3-di-$C_{1-6}$-alkyl-8-(p-sulfophenyl)x- anthines, where the phenyl group in these compounds may be substituted with a halogen (Cl, Br, I), amino, COOH, SO₃, OH or C₁₋₆-alkyl groups.

Preferred adenosine antagonists have the structure shown below:

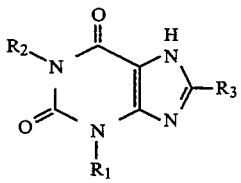

where R₁ is C₁₋₆ alkyl (preferably methyl, ethyl or propyl), R₂ is C₁₋₆ alkyl (preferably methyl, ethyl or propyl) and R₃ is a substituent having a free amino group available for bonding to the carboxylate group of a carboxylate modified microbead. Suitable substituents R₃ include amino, phenylamino, NH₂CHCH₂NH₂, —C₆H₅—O—CONH(CH₂)$_q$NH—(COCH₂—C₆H₅—)$_r$—NH₂, where q=1-6 and r is ) or 1. Methods for synthesizing suitable adenosines antagonists are known. See for example R. F. Bruns, *Biochem. Pharm.*, 30:325-333 (1981); Jacobson et al, *J. Med. Chem.*, 32:1043-1051 (1989); Daly et al, *J. Med. Chem.*, 28:487 (1985); Stiles et al, *Molec. Pharm.*, 32:184-188 (1987); Jacobson et al, *Molec. Pharm.*, 29:126-138 (1986); and Jacobson et al, *Proc. Natl. Acad. Sci. USA*, 83:4089 (1986).

Specific adenosine antagonists which may be used in the present invention include aminophylline; 1-allyl-3,7-dimethyl-8-phenylxanthine; theophylline ethylenediamine; 1-allyl-3,7-dimethyl-8-sulphoxanthine; 7-(β-chloroethyl)theophylline; 4-amino-N-[2-[[[4-(2,3,6,7-tetrahydro-2,6-dioxo-1,3-dipropyl-1H-purin-8yl)-phenoxy]acetyl]amino]ethyl benzeneacetamide; 8-[4-[[[[(aminoethyl)amino]carbonyl]methyl]oxy]phenyl]-1,3-dipropylxanthine; 8-cyclopentyl-1,3-dimethylxanthine; 8-cyclopentyl-1,3-dipropylxanthine; 1,3-diethyl-8-phenylxanthine; 1,3-dimethylxanthine (theophylline); 1,7-dimethylxanthine (paraxanthine); 3,7-dimethylxanthine (theobromine); 1,3-dipropyl-7-methylxanthine; 1,3-dipropyl-8-p-sulfophenylxanthine; 1,3-dipropyl-8-(2-amino-4-chlorophenyl)-xanthine; 3,7-dimethyl-1-propargyl xanthine; PACPX; 7-(β-hydroxyethyl)theophylline; 3-isobutyl-1methylxanthine; 8-[4-[[[[2-(4-aminophenylacetylamino)ethylamino]carbonyl]methyl]oxy]phenyl]-1,3-dipropylxanthine (PAPA-XAC); 8-phenyltheophylline; 3-(n-propyl)-xanthine (enprofylline); 8-(p-sulfophenyl)-theophylline; and xanthine amine cogener (XAC).

When R₃ is amino or phenylamino, a spacer molecule may be optionally used to covalently bind the adenosine antagonist to the carboxylate modified microbead. The spacer compounds noted above for use with adenosine agonists are also suitable for use with the adenosine antagonists in which R₃ is amino or phenylamino.

Generally, freshly activated microbeads are added to an alcohol/water or dimethylsulfoxide/water mixture and the adenosine agonist or antagonist is then charged into this mixture and stirred to allow amide bond formation. The adenosine derivative coupled to the microbead can be readily obtained by centrifuging the resulting solution. Suitable alcohols include C₁₋₆-alkanols, preferably ethanol or isopropanol. Generally, a slight excess of the adenosine derivative is added relative to the surface charge equivalent of the microbead to provide high yields of the coupled product.

Dextrans suitable for use in the present invention are dextrans having a molecular weight ranging from 1,000 Daltons to 5,000,000 Daltons (1-5,000 kD). Suitable dextrans are commercially available (Sigma Chemical Co.) having a wide range of average molecular weights. Dextrans having a specific average molecular weight range are purified with dialysis to exclude low molecular weight contaminants. Preferred high molecular weight dextran has a molecular weight of about 1,000,000-2,000,000 Daltons (1,000-2,000 kD). Preferred low molecular weight dextrans have a molecular weight of about 1,000-10,000 Daltons (1-10 kD).

The adenosine derivative can be covalently coupled to the dextran by any known coupling reaction to produce a covalent bond which is stable under physiological conditions. A preferred method of covalently bonding the adenosine derivative to the dextran is analogous to the cyanogen bromide method of Axen et al, *Nature*, 214:1302 (1967) to bind protein to oligosaccharides. In this method, a dilute aqueous solution of the dextran is reacted with cyanogen bromide to form cyanate groups while maintaining a basic pH through the addition of dilute sodium hydroxide. The activated dextran containing reactive cyanate groups may be used for direct coupling to the desired adenosine derivative.

Reaction of the activated dextran with an adenosine derivative having a free amino group is believed to form a carbamate linkage between the dextran and the adenosine derivative (Axen et al). See also Armstrong et al (*Biochem. Biophys. Res. Comm.*, 47:354-360 (1972)).

The intravascular perfusion of high molecular weight adenosine agonists (about 1,000,000 Daltons or more) and adenosine agonists bound to microbeads cause coronary dilation, a negative dromotropic effect and depression of spontaneous ventricular rhythm. Since the high molecular weight compounds remain in the vascular lumen, these effects are thought to be the result of activation of intravascular endothelial receptors by the adenosine agonist.

Figure 2A:
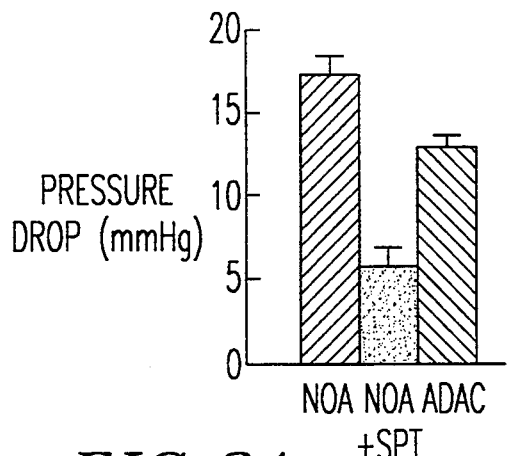
FIGS. 2(A) and 2(B) show the decrease in coronary perfusion pressure and ventricular developed pressure induced by adenosine agonist derivatives (NOA and ADAC)
Figure 2B:
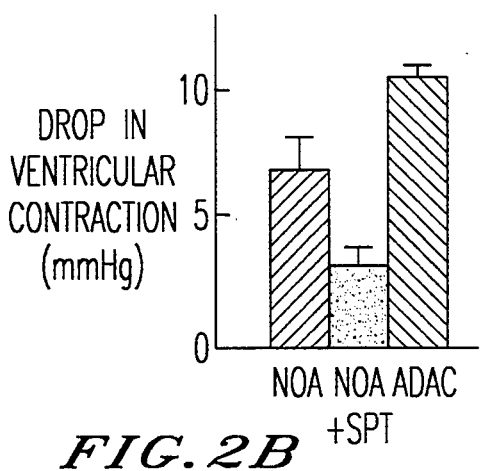

In hearts perfused at a constant coronary flow, intracoronary perfusion of microbead (microsphere) bound agonists produce coronary dilation resulting in a decrease in coronary perfusion pressure and in ventricular developed pressure as shown in FIGS. 2(A) and 2(B). These effects are reversible and are inhibited by the adenosine receptor blocker 8-sulphophenyltheophylline (SPT). The mean decrease in coronary perfusion pressure (control =49 ±1.7 mmHg) and ventricular developed pressure (control =65 ±3.5 mmHg) from several experiments with microbead (microsphere) bound NOA (SPH-NOA) and microbead (microsphere) bound ADAC (SPH-ADAC) are shown in FIGS. 2(A) and 2(B). These changes were statistically significant with a value of p<0.05. Perfusion with control microbeads did not exhibit these effects.

Figure 2C:
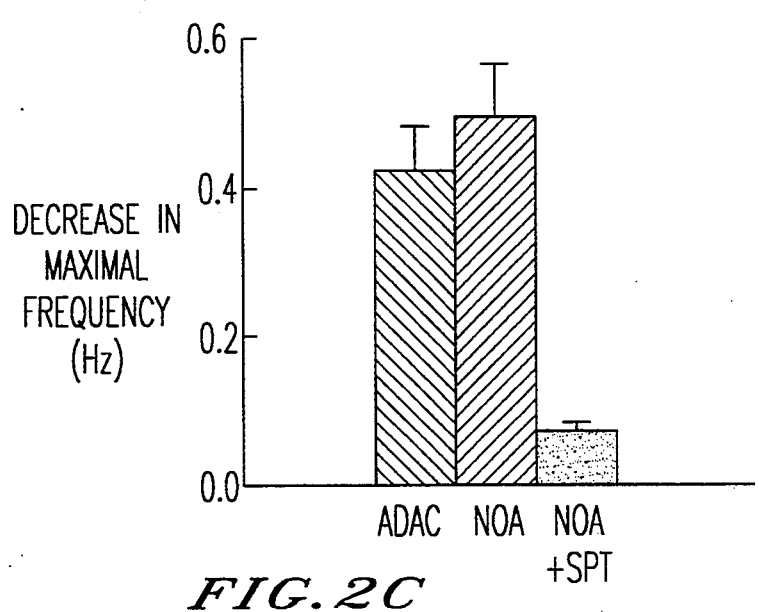
FIG. 2(C) shows a decrease in the maximal frequency of atrial pacing to producing a 1:1 A-V propagation induced by microbead coupled NOA or microbead coupled ADAC, and the blockade of the microbead-coupled NOA effect by SPT.
Figure 3A:
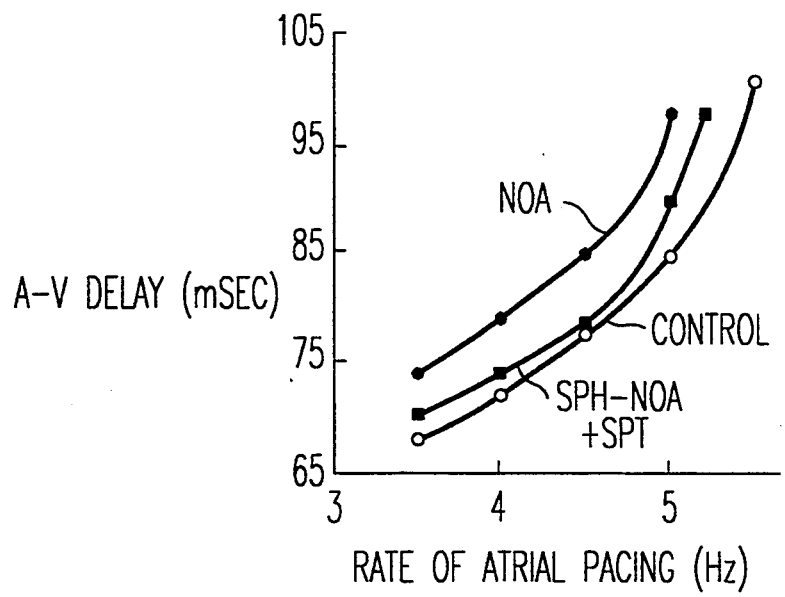
FIG. 3(A) and FIG. 3(B) show the negative dromotropic effect caused by intracoronary infusion of microbead-coupled NOA and the blockade of this effect by SPT, A-V delay (ordinates) at different frequencies of atrial pacing (abscissas)
Figure 3B:
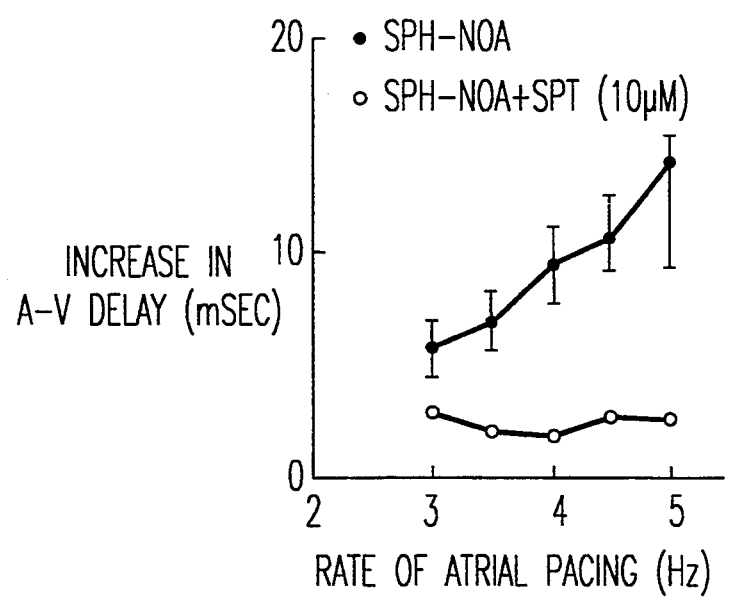
Figure 4A:
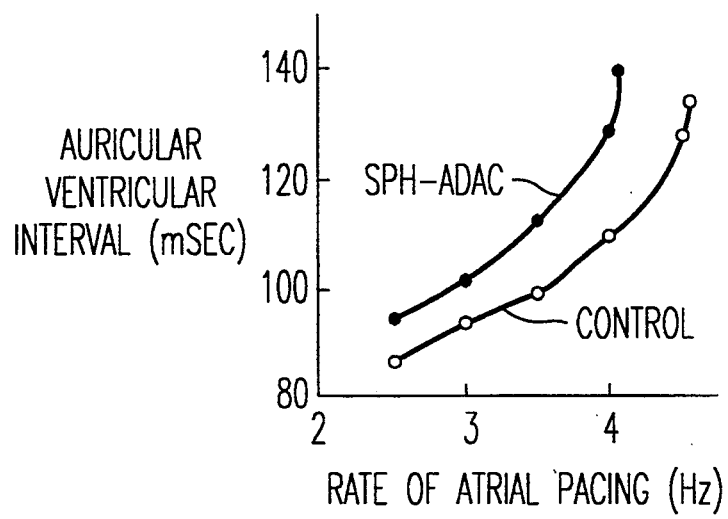
FIG. 4(A) and FIG. 4(B) show the negative dromotropic effect caused by intracoronary infusion of microbead-coupled ADAC, A-V delay (ordinates) at different frequencies of atrial pacing (abscissas)
Figure 4B:
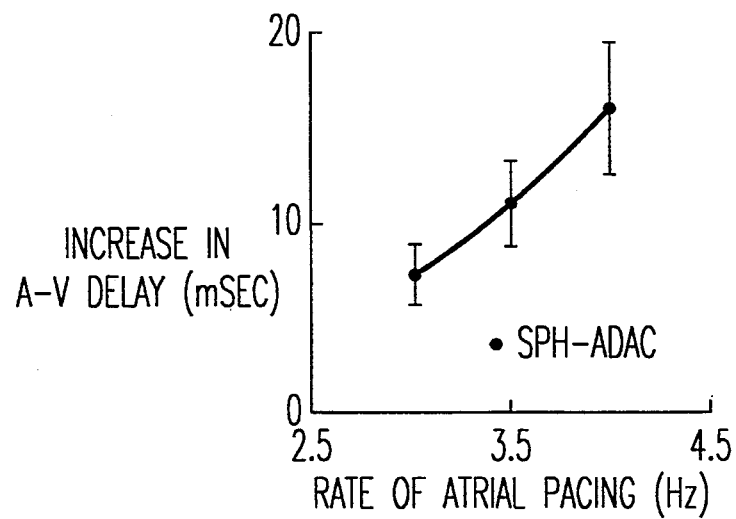
Figure 5:
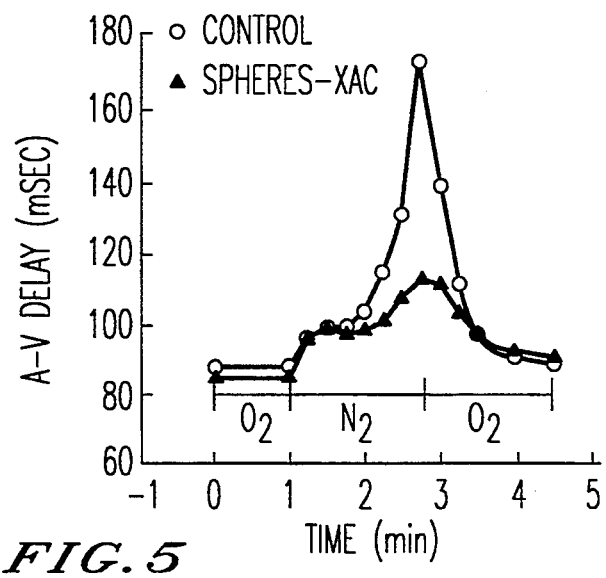
FIG. 5 shows a selective blockade of the hypoxia-induced lengthening in A-V delay by intracoronary infusion of microbead-coupled XAC.

Perfusion with microbead-bound agonists also causes a negative dromotropic effect, These compounds cause a shift upward and to the left of atrial-ventricular (A-V) delay-atrial frequency curves as shown in FIGS. 3(A) and 4(A). At any frequency of atrial pacing, the A-V delay was lengthened and the maximal frequency of atrial pacing to yield a 1:1 A-V transmission was reduced. These effects were inhibited by SPT as shown in FIG. 3(A). FIGS. 3(B) and 4(B) plot the differences between experimental values and corresponding control values of A-V delays at various frequencies of atrial pacing. The mean values of several experiments were statistically significant for all points at a $p \leq 0.02$. The differences between control maximal frequency of atrial pacing for a 1:1 A-V transmission (mean=5.1 ±0.04 Hz) minus the corresponding experimental maximal frequencies for SPH-NOA and SPH-ADAC are shown in FIG. 2(C). All values have a statistical significance of $p \leq 0.01$. Perfusion with control microbeads did not exhibit these effects.

Figure 2D:
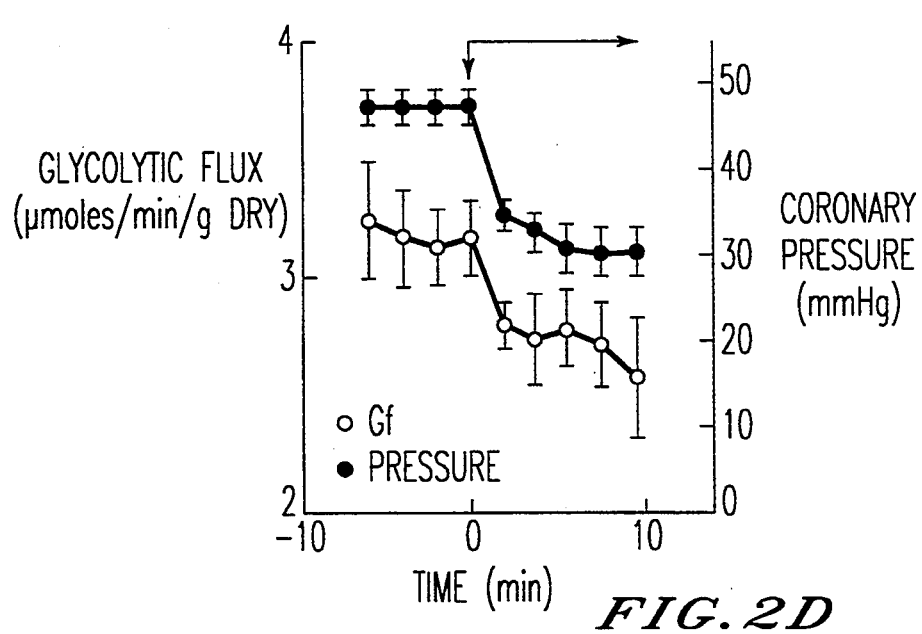
FIG. 2(D) shows the decrease in glycolytic flux and coronary perfusing pressure caused by sustained infusion of microbead-coupled NOA.

Infusion of the agonists of the present invention also effects the spontaneous ventricular rhythm and glycolytic flux. Intracoronary infusion of SPH-NOA caused the rate of spontaneous ventricular rhythm to drop from a control value of 149±9 to 116±2 beads/min ($p \leq 0.01$). Upon termination of SPH-NOA infusion, spontaneous ventricular discharge recovered to the initial control value. FIG. 2(D) shows that intracoronary infusion of SPH-NOA causes a significant reduction in glycolytic flux ($p \leq 0.05$). Perfusion with control microbeads did not affect spontaneous ventricular rhythm of glycolytic flux.

Figures 6A, 6B, 6C:
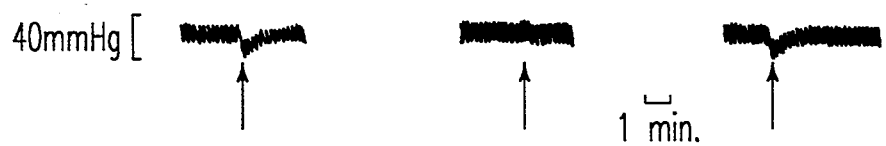
FIG. 6 shows the effect of 10 $\mu$l adenosine boluses ($10^{-3}$M, shown by arrow) on mean coronary perfusion pressure at a constant coronary flow of 10 ml/min.
Figure 6D:
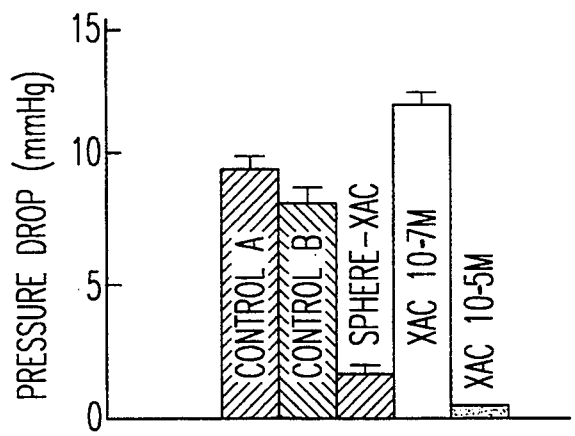
Figure 6E:
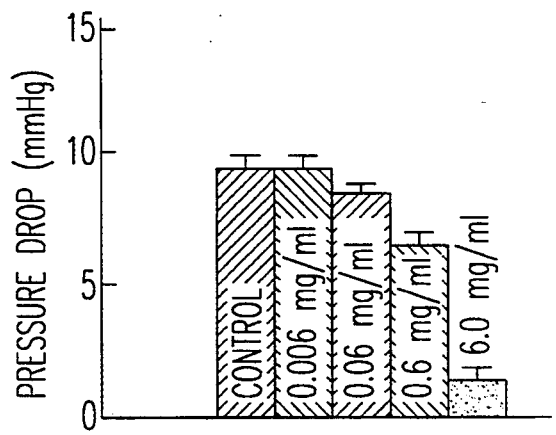

Bolus injections of adenosine allow one to assess the ability of the antagonist derivatives of the present invention to block adenosine $A_1$ receptors. FIG. 6(A) shows the rapid drop in mean coronary pressure caused by administration of a 10.0 μl adenosine bolus ($10^3$M) with subsequent recovery. The vascular response was resistant to bolus injections of adenosine ($p<0.001$) during infusion of SPH-XAC (6.0 mg/ml) as shown in FIG. 6(B). With an equivalent molar amount of free XAC ($10^{-7}$M), the vascular response to adenosine bolus injection was not blocked as shown in FIG. 6(C). The vascular response was affected only in that the magnitude of the coronary pressure drop was greater ($p<0.05$) due to a higher baseline mean coronary pressure observed during free XAC infusion. Only at concentrations of $10^{-5}$M free XAC, was there a complete block of the mean coronary pressure drop with adenosine bolus injections. See FIG. 6(D), $p<0.0001$. The 100 fold difference in pharmacological effect between microbead bound XAC and free XAC is illustrated in FIG. 6(E) where infusion of 0.06 mg/ml microbead-XAC did not block the vascular effects of adenosine bolus injection.

Figure 7A:
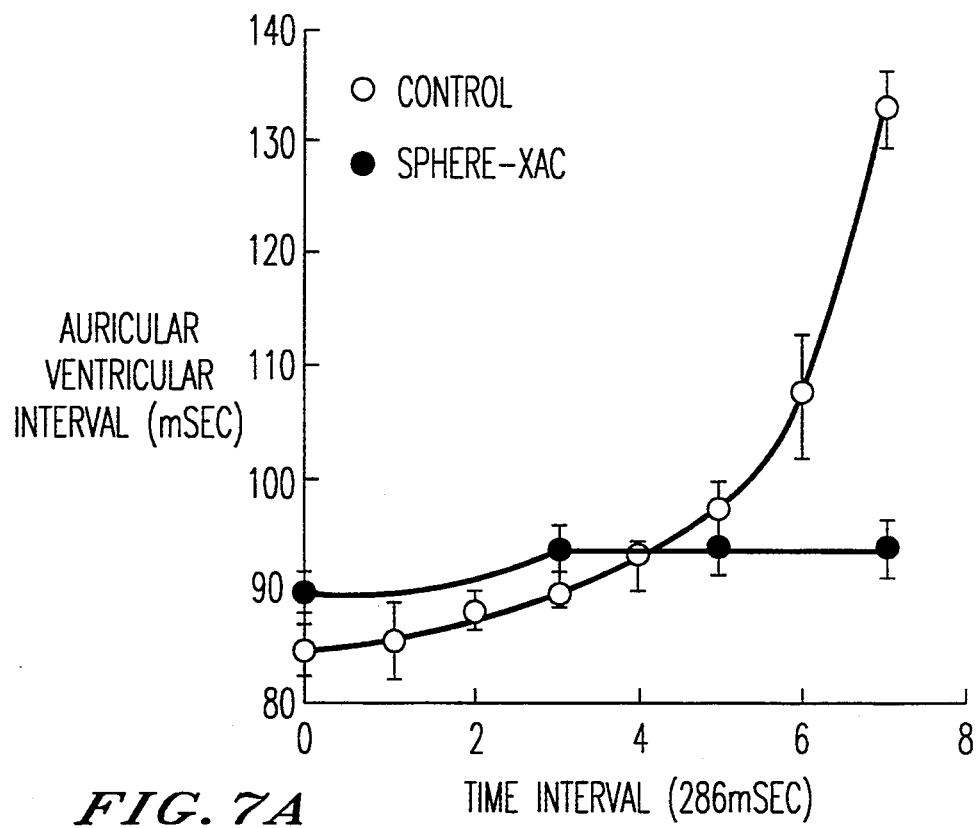
FIG. 7(A) : effect of SPH-XAC (6.0 mg/ml, n=6) infusion.
Figure 7B:
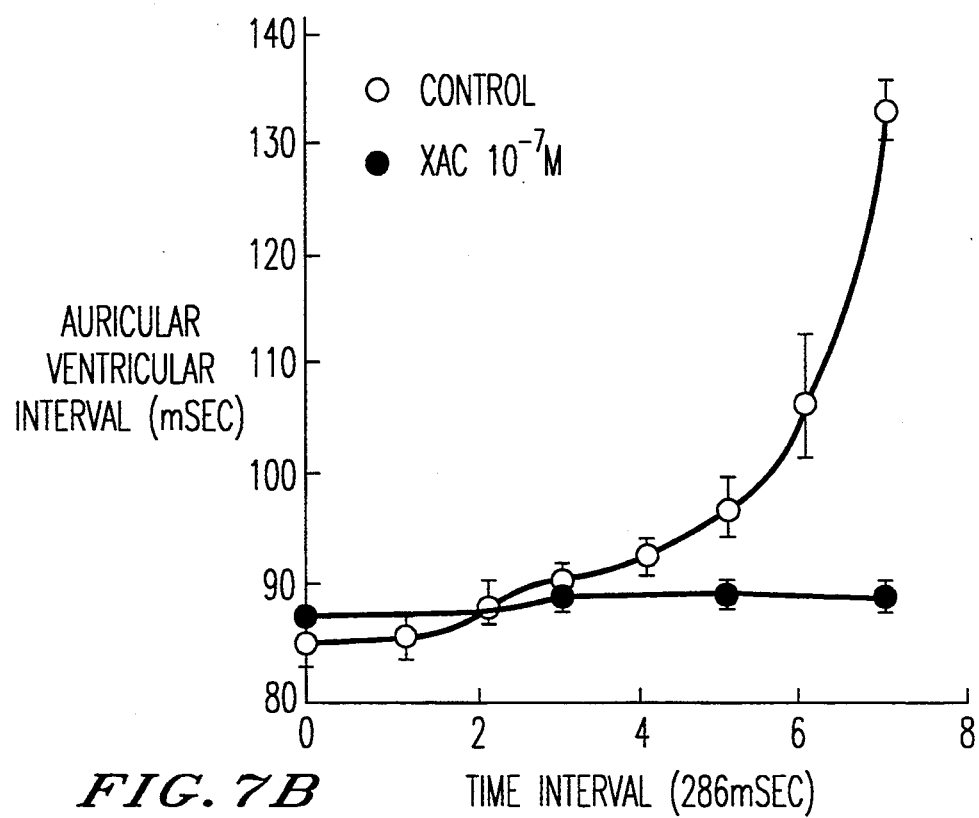
FIG. 7(B): effect of XAC $10^{-7}$M (n=6) infusion. Controls in FIG. 7(A-B) are K-H perfusion only (n=7)

There is no pharmacological difference in dromotropic effects between microbead-XAC and free-XAC. See FIGS. 7(A) 7(B), where equivalent molar amounts of microbead-XAC and free-XAC both block the negative dromotropic effects of adenosine bolus injections.

Figure 8A:
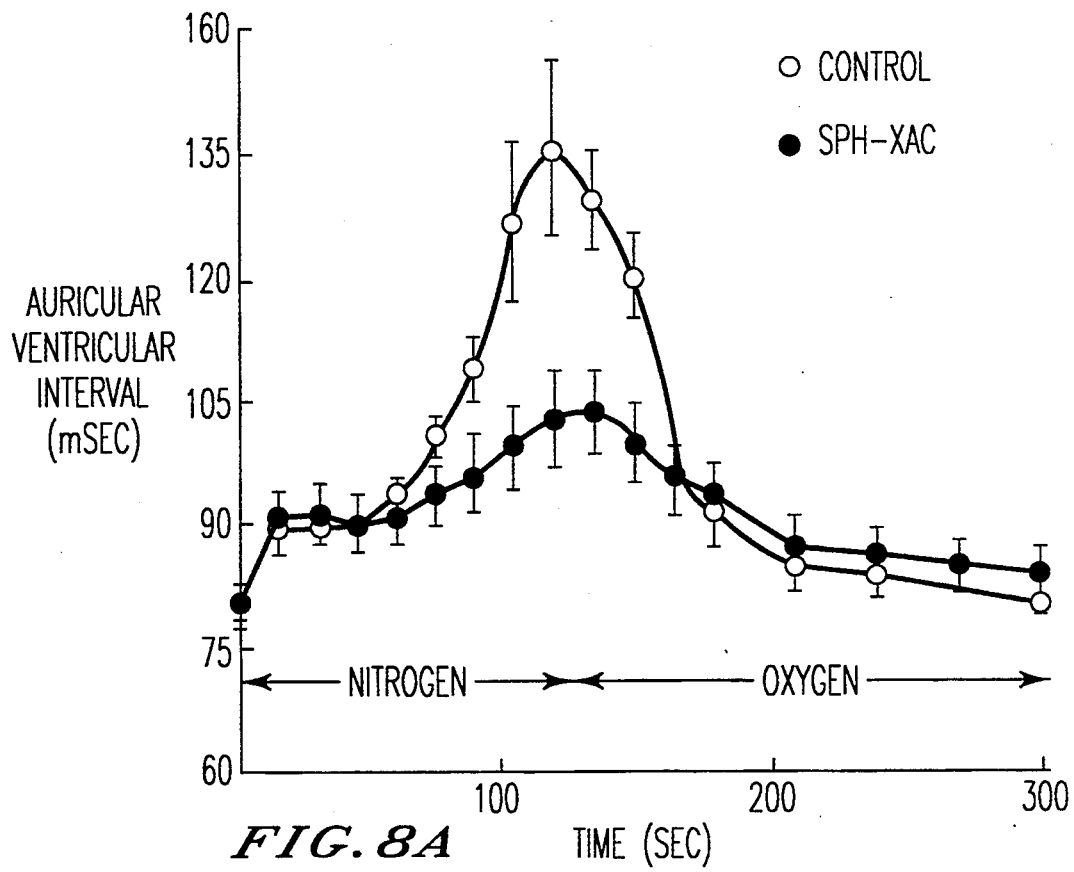
FIG. 8(A): control (n=8) and during 6.0 mg/ml SPH-XAC (n=7) infusion.
Figure 8B:
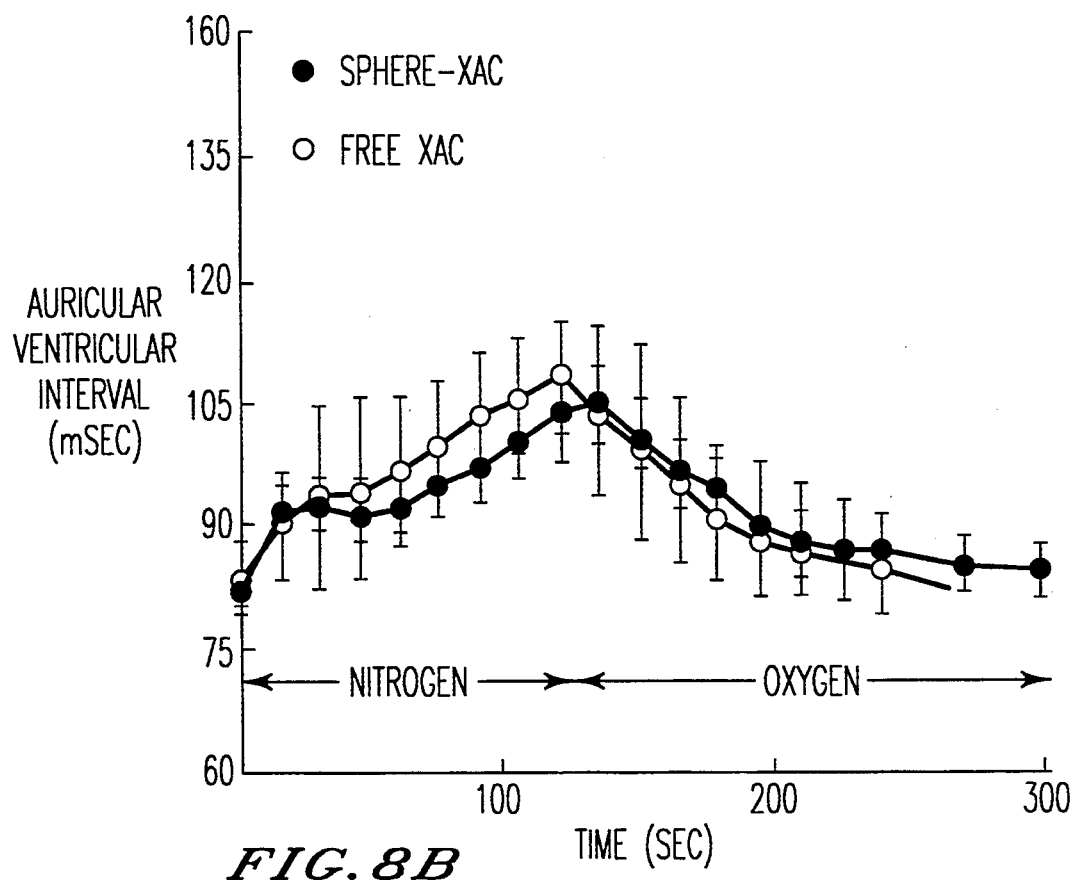
FIG. 8(B): comparison during infusion of XAC $10^{-7}$M (n=4) and during infusion of 6.0 mg/ml SPH-XAC.

FIGS. 8 and 9 show the dromotropic and vascular effects of the microbead-bound antagonists of the present invention under hypoxic conditions. FIGS. 8(A) and 8(B) show the dromotropic effects of a 2.0 minute period of perfusion with K-H equilibrated with 95% $N_2$+5% $CO_2$ where the maximal prolongation of the A-V interval is reduced by greater than 50% (p <0.01) during infusion of equal molar amounts of free and microbead-XAC.

The vasodilatory effects of endogenous adenosine were studied under two varying degrees of hypoxia (0% $O_2$ and 20% $O_2$) in order to assess whether the degree of hypoxia would reveal any differential effect between equal molar amounts of microbead-XAC and free-XAC. FIG. 9 shows that during an individual experiment (FIGS. 9(A-C)) the mean coronary pressure drop decreased by a similar magnitude whether microbead-XAC or free-XAC was infused. Neither compound significantly blocks the vasodilatory effects of hypoxia. There is no statistical difference between the control and experimental conditions during maximal levels of hypoxia as shown in FIG. 9(D) at 0% $O_2$ or minimal levels of hypoxia as shown in FIG. 9(E) at 20% $O_2$.

The adenosine derivatives covalently coupled to microbeads of the present invention have the advantage that these particles are confined solely to the intravascular compartment. However, the colloidal nature of these microbead-bound pharmaceuticals results in a low effective concentration due to the insolubility of the particles in the aqueous blood system. The dextran-coupled adenosine derivatives of the present invention are medium and large water soluble compounds, however, and have a substantially higher effective concentration.

Figure 10A:
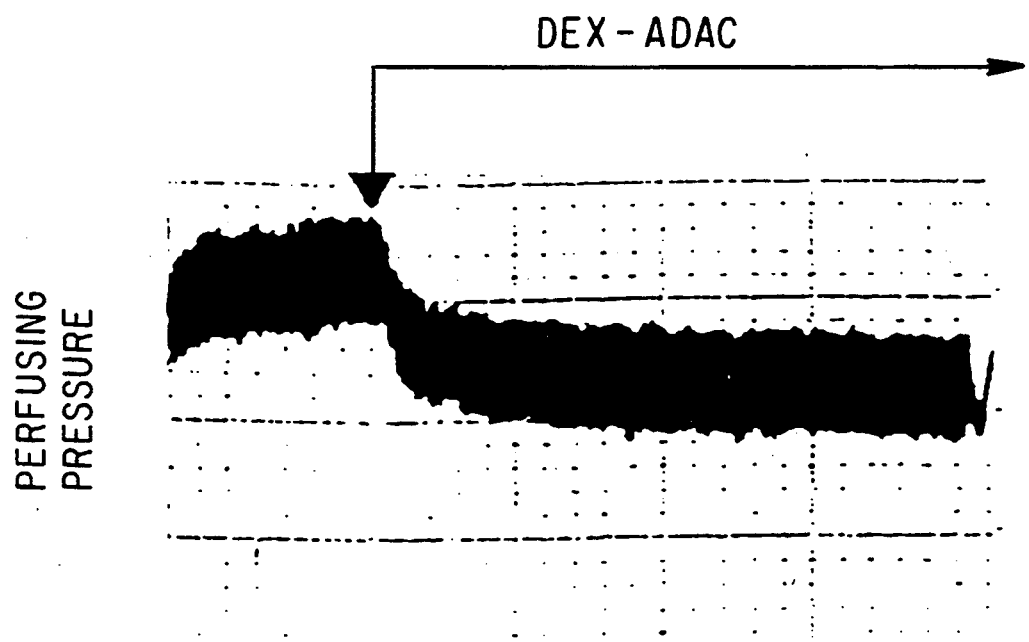
FIG. 10 shows the results of an individual experiment in which intracoronary perfusion of dextran-coupled ADAC produced a decrease in coronary perfusion pressure and in ventricular developed pressure.
Figure 10B:

As with microbead-bound adenosine derivatives, the dextran-bound derivatives also cause a decrease in coronary perfusion pressure and in ventricular developed pressure. The results of an individual experiment with dextran-ADAC are shown in FIG. 10. Similar results are obtained with dextran-NOA perfusion.

Sustained intracoronary infusion of dextran-ADAC causes a gradual rise in the A-V delay (FIG. 11) similar to A-V delay results observed with microbead-ADAC.

Figure 11:
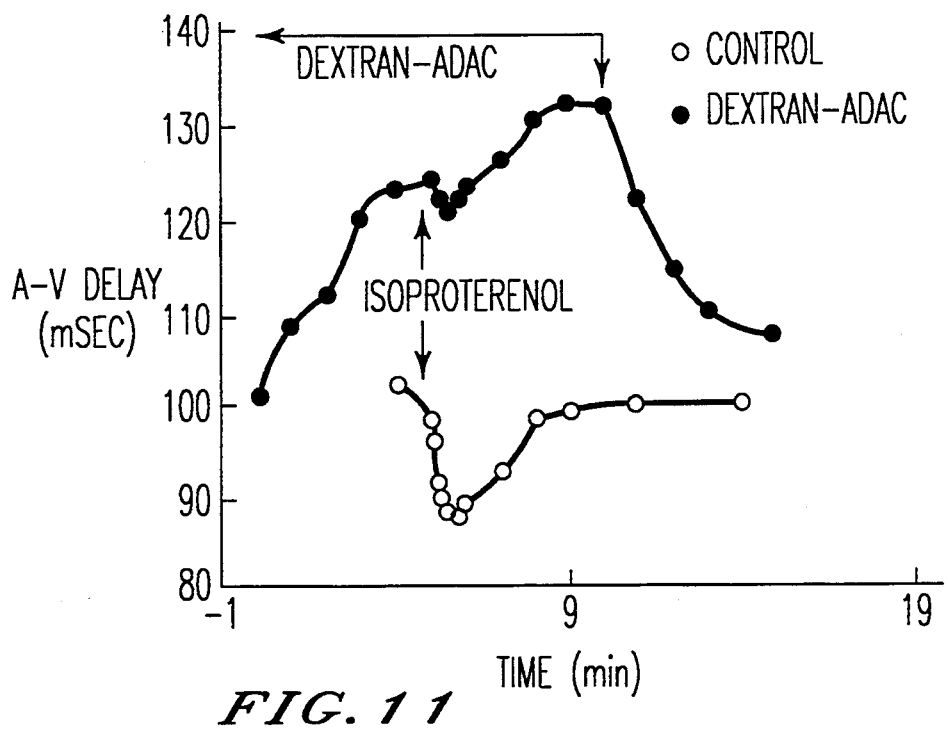
FIG. 11 shows the results of sustained intracoronary infusion of dextran-coupled ADAC on A-V delay.

FIG. 11 shows the anti-adrenergic effect of dextran-ADAC. During perfusion of dextran ADAC (0.1 mg/ml), a bolus of isoproterenol (0.0001 μg) was administered. The positive dromotropic effects of isoproterenol were considerably depressed and shorter than when isoproterenol was given alone. See the lower trace in FIG. 11. Termination of the dextran-ADAC infusion reversed the negative dromotropic effects.

Figure 12:
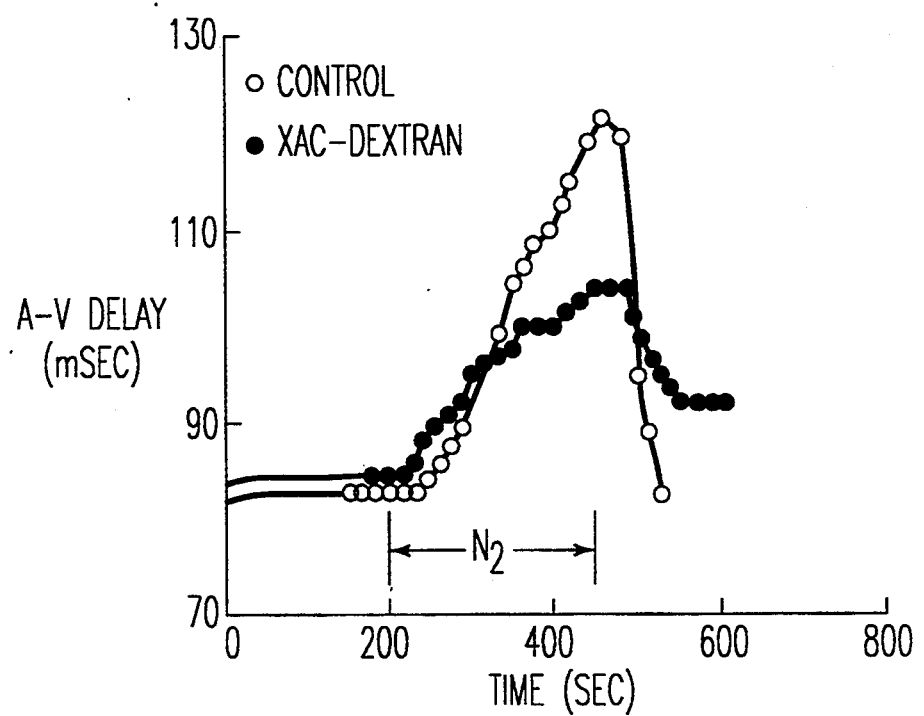
FIG. 12 shows that upon perfusion with a hypoxic medium, A-V delay lengthens and upon reoxygenation, this effect is reversed (control). However, if the same insult is applied during a sustained infusion of dextran-XAC (0.1 mg/ml), the hypoxic effect is substantially blocked.

As noted above, hypoxia causes an increase in the A-V delay which has been attributed to a rise in the interstitial levels of adenosine, which act directly on A-V nodal cells depressing the generation of their action potentials. This effective adenosine is blocked by methylxanthines. The negative dromotropic effects of hypoxia are blocked by 0.1 mg/ml dextran-XAC (FIG. 12).

Adenosine antagonists coupled to high molecular weight dextrans or microbeads have only minor coronary and dromotropic effects when administered intracoronarily. These adenosine antagonists (at 0.01 to 10 mg/ml) block hypoxia-induced lengthening of the auricular-ventricular interval without affecting the associated coronary dilation. Using high molecular weight compounds, therefore, one is able to cause prolonged coronary dilation, a negative dromotropic effect and depress spontaneous ventricular rhythm in mammals.

The high molecular weight adenosine agonists of the present invention are useful in treating hypertension, cardiac arrhythmias and in preserving myocardial tissue. Infusion of high molecular weight agonists (at 0.01 to 10 mg/ml) results in coronary dilation and a drop in intravascular pressure (blood pressure), offering a selective treatment for hypertension. The negative dromotropic effect of the high molecular weight agonists (at 0.1 to 10 mg/ml) can be used to treat tachycardiarrhythmias, such as supraventricular tachycardia. Infusion of the high molecular weight adenosine agonist increases the A-V interval thereby offering effective treatment for tachycardia.

Additionally, the adenosine agonists (at 0.1 to 20 mg/ml) of the present invention are useful in reducing the size of a myocardial infarction in the same manner in which adenosine itself is used to reduce infarct size and improve regional ventricular function in ischemic zones of the heart. See Olafsson et al, Babbit et al and Liu et al.

The covalently coupled adenosine agonists and antagonists of the present invention may be administered by intracoronary infusion at an intracoronary infusion concentration of about 0.01 mg/ml to about 20 mg/ml, preferably about 0.05–0.50 mg/ml. The solutions or suspensions of covalently coupled adenosine agonists and antagonists are preferably continuously infused.

Pharmaceutical compositions containing the covalently coupled adenosine derivatives are also within the scope of the present invention. The pharmaceutical compositions include solutions or suspensions of the covalently coupled adenosine agonist or antagonist in a sterile saline or buffer solution suitable for infusion into the patients vascular system. Solutions or suspensions in sterile 5% saline, dextrose-5%-saline or phosphate buffered saline solutions having a concentration of about 0.01 mg/ml to about 20 mg/ml, preferably about 0.05–0.50 mg/ml of the covalently coupled adenosine agonist and/or antagonist are preferred. These pharmaceutical compositions may be administered repeatedly by intravenous injection or continuously by slow intravenous infusion.

Other features of the invention will become apparent during the course of the following descriptions of exemplary embodiments which are given for illustration of the invention and are not intended to be limiting thereof.

EXAMPLES

I. Microbead Coupling

Activation of microbeads. Carboxylate modified beads with a surface charge density of 0.3 meq/g and mean diameter of 0.07 μm (Seradyn Inc.) were prepared by diluting to less than 5% solids with deionized water. The solution was stirred for 2 hours with a 50/50 anionic/cationic exchange resin at a 2:1 wt/wt ratio of resin to beads. Resin was removed, thereafter, the pH of the filtered colloidal mixture was titrated with 1.0M NaOH to a value of 7.5. The microbeads were then activated at 4° C. with 1-(3-dimethyl-aminopropyl)-3-ethyl carbodiimide in a 5:1 mole ratio followed by the addition of N-hydroxysuccinimide in a 4:1 mole ratio in order to stabilize the O-acylurea activated intermediate. This mixture was then ready for direct coupling.

$N^6$-octylamine adenosine (NOA) conjugation to activated microbeads. To freshly activated microbeads was added isopropyl alcohol and deionized water to create a 50/50 mixture of 15 ml with 100 mg beads per total volume mixture. This solution was cooled to 4° C. and charged with NOA at a 1.5/1.0 mol ratio of adenosine agonist to surface charge equivalents. The solution was vortexed at 5 minute intervals for 20 minutes and allowed to stand at 4° C. overnight. The reaction mixture was then centrifuged at 40,000×g for three hours, and the supernatant was decanted and resuspended in deionized water with a microtip sonifier. This purification procedure was repeated 5 times. Prior to coronary infusion, these spheres were resuspended in deionized water at a concentration of 5–6 mg/ml.

$N^6$-[4-(2-Aminoethylaminocarbonylmethyl)phenyl]adenosine (ADAC) conjugation to activated microspheres. The activated microsphere suspension was diluted with DMSO and deionized water to create a 70/30 v/v mixture respectively at a total volume of 30 ml/100 mg spheres. A concentrated stock solution of ADAC was prepared in a DMSO deionized water mixture (70/30 v/v respectively) and this ADAC solution was added to the microsphere suspension a 1.5/1.0 mol ratio of ADAC to surface charge equivalents. The reaction time was 2 h at 4° C. The reaction mixture was then dialyzed for 10 h at 4° C. against deionized water through a dialysis membrane with a cutoff at 14,000–16,000. This purification step was repeated four times. In order to concentrate the spheres prior to its use, after the last dialysis step the sphere suspensions were centrifuged at 40,000×g for 3 h, the fluid was decanted and spheres resuspended in deionized water at a concentration of 5–6 mg/ml. In all experiments microbeads were intracoronarily infused at a concentration of 0.05 mg/ml.

In order to test for the presence of free agonist in the sphere-agonist suspension, an aliquot of this suspension was filtered through a centrifugal ultrafiltration unit with a cutoff of 30,000 kD (Millipore ULTRAFREE-20 filter unit, 10,000 NMWL). This step retained the microbeads particles in the filter and resulted in a microbead free filtrate that could only contain free agonist.

8-[4-(2-aminoethylaminocarbonyl methoxy)phenyl]-1,3-dipropylxanthine (XAC) conjugation to activated microbeads. 5.0 mM XAC (RBI) solutions were prepared in 0.1N NaOH and 1.0% NaCl, and subsequently was titrated to pH 9.2 with 0.1M HCl prior to use. This XAC solution was then added to the microbead suspension in a 1.0/1.0 mole ratio of XAC to microbead-surface charge equivalents. The reaction time was carried out overnight at 4° C. The reaction mixture was then dialyzed for 48 hours at 4° C. against deionized water through a dialysis membrane with a molecular weight cutoff at 14,000–16,000. The bead-XAC solution was then centrifuged at 10,000×g for 10 min. in order to remove excess precipitate and was followed by 6 successive centrifuge washings at 40,000×g in order to remove low molecular weight contaminants. In the case of the washings, the pelleted microbeads were each time resuspended in deionized $H_2O$ with a microtip sonifier. In all experiments microbeads were infused at a concentration of 6.0 mg/ml, and as the microbeads were infused at a rate of 0.1 ml/min. and diluted with perfusion media at a rate 10.0 ml/min., the final intracoronary concentration was 0.06 mg/ml. In all further reference to microbead concentration, it is the infusion concentration which is expressed.

The efficiency of the conjugation reaction was determined by spectrophotometric means and by radioisotope spiking of reaction media with $^3H$ labeled XAC (NEN Research Products) followed by scintillation counting of the purified reaction product. For the spectrophotometric quantification of covalently bound XAC it was necessary to dissolve the microbead conjugates in pyridine in order to eliminate the scattering effects of the microbeads.

In order to test for the presence of "free" antagonist in the bead-antagonist suspension, an aliquot of this suspension was filtered through a centrifugal ultrafiltration unit with a cutoff of 30 kD (Millipore ULTRAFREE-20 filter unit, 10,000 NMWL). This step retained the microbead particles in the filter and resulted in a microbead free filtrate that could only contain "free" antagonist.

Two types of control beads were prepared either omitting: a) 1-(3-dimethylaminopropyl)-3-ethyl carbodiimide during the activation step or b) the conjugation moiety. In all experiments microbeads were intracoronarily infused at a concentration of 0.06 mg/ml.

II. Dextran Coupling

Activation of Dextran. The cyanogen bromide method was used for all dextran conjugation reactions. The dextran was purified by dialysis (dialysis membrane cutoff 16 kD) to exclude small molecular weight contaminants. Subsequently a stirred solution of 0.01% dextran was charged with cyanogen bromide in 3 equal portions at 15 min. intervals, to yield a final 50 wt/wt % of cyanogen bromide to dextran solution. The pH of this activation step was monitored constantly and maintained at pH 10.7 by addition of 1M NaOH. Thirty min. after the addition of the last cyanogen bromide portion, the solution was used for direct coupling.

$N^6$-[4-(aminoethylamino)carbonylmethylphenyl-]adenosine (ADAC) conjugation to activated dextran. Reaction with ADAC proceeded as above for direct coupling of ADAC to activated microbeads, except ADAC was added at a 50 wt/wt % to dextran, and the ADAC was solubilized in 0.1M acetic acid. Coupling time and purification were same as above except that final dialysis was against 0.9% saline solution.

XAC conjugation to activated dextran. XAC was solubilized in 0.1M NaOH and coupled to activated dextran according to the procedure disclosed above.

III. Microbead Experiments

Isolated saline perfused hearts. Male guinea pig (350–400 g) were anesthetized with an intraperitoneal injection of ketamine/xylazine (80/20 mg/Kg body weight) and heparin (500 U). The heart was removed and retrogradely perfused via a non-recirculating perfusion system at constant flow. Perfusion was initiated at a rate of 25.0 ml/min for 5.0 minutes and followed by 25.0 min equilibration period of perfusion at a rate of 10.0 ml/min. All experimental measurements were initiated after this period of equilibration. The perfusion media was Krebs-Henseleit solution (K-H) with the following composition (mM): NaCl 117.8, KCl 6, $CaCl_2$ 1.6, $NaHCO_3$ 25, $NaH_2PO_4$ 1.2, NaEDTA 0.0027, and glucose 5.0. This solution was equilibrated with 95% $0_2$, 5% $CO_2$ at 37° C. and had a pH of 7.4. Subsequent studies during induced hypoxia used an equilibrated perfusion media with either (95% $N_2$+5% $CO_2$) or (75% $N_2$+20% $O_2$+5% $CO_2$).

All experiments were performed at a constant coronary flow of 10.0 ml/min and the coronary perfusing pressure was recorded continuously via a side arm of the perfusing cannula and had a control value of 48±2.5 mmHg.

One pair of stimulating electrodes was placed in the apex of the right atria and electric square pulses of 2.0 msec duration and two times threshold were applied. To record the electrocardiogram one electrode was placed in the right atria and a second electrode in the left ventricle. These two electrodes were connected to an oscilloscope synchronized with the atrial pacing stimulator while the auricular-ventricular delay (A-V delay; msec) was continuously monitored and measured as the time interval between the application of the stimulus to the atria and the initiation of the rising phase of the ventricular electrical signal. The time between the application of the stimulus and the atrial electrogram remained constant (18±1.3 msec) throughout all the experimental manipulations.

Measurements of A-V delay during adenosine bolus experiments were performed with the aid of a polaroid camera mounted on the oscilloscope display panel. Manual operation of the shutter speed was sufficient to capture A-V delay prior to the gradual development of complete heart block (Mobitz type 11); so that each filmed exposure contained successive electrocardiographic tracings where each beat (occurring at a time equivalent to 1/[stimulation frequency]) showed the gradual prolongation A-V delay to complete heart block.

Studies during hypoxia with microbead-XAC. The effect of hypoxia on coronary pressure and A-V delay were studied under control conditions and during constant infusion of "unbound" XAC and "microbead-bound" (bead-XAC) XAC. These studies were performed at two levels of reduced oxygen tension. For control experiments the K-H solution was equilibrated with 95% $O_2$+5% $CO_2$ and subsequent hypoxic studies with 95% $N_2$+5% $CO_2$ or 75% $N_2$ +20% $O_2$+5% $CO_2$. In all cases hypoxic conditions were initiated, after 25 min. of equilibration during control conditions, by rapid-manual switching to a parallel perfusion system equilibrated with the appropriate gas mixture. Hypoxic conditions were maintained for 2.0 minutes in all experiments. Thereafter, coronary pressure and A-V delay were continuously monitored as a function of time. A structural dead space in our perfusion apparatus, of approximately 2.0 ml, was responsible for the aberrant cardiovascular effects seen in the initial one minute during hypoxia.

Electronmicroscopy. Electronmicroscopy studies were conducted to demonstrate that the 0.07 $\mu m$ diameter microbeads when infused intracoronarily remained confined to the intravascular space. As described above, the hearts were isolated and perfused with K-H at a rate of 10.0 ml/min and infused with the microbeads (6.0 mg/min ) at a rate of 0.1 ml/min. for 5.0 min. Thereafter, while the infusion of microbeads was sustained, the perfusion with the K-H solution was changed to one of glutaraldehyde (50 mM phosphate buffer, pH 7.4, glutaraldehyde 2.5%) and perfused at the same rate for a period of 10.0 min. The heart was removed and the free wall of the left ventricle was minced into small cubes of 1.0 MM3 and left overnight in the glutaraldehyde solution. The ventricular tissue was then rinsed in phosphate buffer and post fixed for 60.0 min in 1% $OsO_4$ solution followed by a water rinse. Following alcohol dehydration, the tissues were embedded in epon resin and sections of 0.6 $\mu m$ to 0.9 $\mu m$ were cut and stained with lead citrate and uranyl acetate. Sections were then viewed and photographed in a transmission electronmicroscope.

The electronmicroscopic studies showed that no microbeads could be observed in the myocardial parenchymal tissue after 5.0 min. of microbead infusion.

Bioassay to detect the presence of free antagonist in venous effluents For these studies two heart preparations were utilized; a "donor" heart from which venous effluent was collected and a "recipient" heart from which venous effluent was assayed. Accordingly, as an index for evaluating the possibility of "hydrolyzed" XAC from bead-XAC conjugates during infusion into the "donor" heart, the dromotropic effects of adenosine bolus injections were evaluated in the "recipient" heart during perfusion with donor effluent. Specifically, a control venous effluent aliquot of 1 00 ml from the "donor" heart was collected prior the coronary infusion of the bead-XAC into the donor heart. Thereafter, in order to determine if the bead-XAC complex was hydrolyzed into free XAC and beads, during its passage through the heart, microbeads were perfused into the "donor" heart and experimental venous effluents were simultaneously collected for about 20 minutes. The experimental venous effluents were divided into two equal volume aliquots. In one of these aliquots the bead-agonist complexes were removed by filtering it first through a membrane of 0.24 μm pore size, thereafter, the filtrate was passed through a centrifugal ultrafiltration unit with a cutoff of 30 kD. This step retained the microbeads particles in the filter and resulted in a microbead free filtrate that could contain only free agonist. The other venous effluent aliquot was assayed with bead-XAC remaining in solution. The different venous effluents from the donor heart were equilibrated with 95% $O_2$+5% $CO_2$ and brought to 37° C. prior their infusion into the "recipient" heart and they were assayed in the following order; control effluent, experimental effluent with removed microbeads and experimental effluent with microbeads. The results show that control and experimental effluents with removed microbeads have no effect in the recipient heart while the experimental effluents with microbeads have the same effects in the recipient heart as in the donor. These results establish the stability of the chemical bond between agonist/antagonist and the microbeads.

Measurements of coronary resistance. Coronary resistance was determined from the ratio of coronary perfusion pressure to coronary flow. In all these experiments coronary flow was maintained constant at 10 ml/min.

Measurements of ventricular contraction (Myc.). Via the left atria a fluid filled balloon was introduced into the left ventricle. Diastolic pressure was adjusted to about 10 mmHg and the developed pressure (Myc, mmHg) continuously determined.

Studies on A-V. A-V delay was determined at various frequencies of atrial stimulation and A-V delay (ordinates)-frequency (abscissas) plots were generated.

Studies on spontaneous ventricular rhythm, ($V_t$). Spontaneous ventricular rhythm was induced by destroying the A-V nodal area. For this purpose, a large incision was made in the right atria to clearly expose the coronary sinus ostium, the ventricular septum and the tricuspid valve. Destruction of the A-V nodal area was achieved by crushing with small forceps the superficial tissue laying between the ostium and cardiac valves. This manipulation resulted in blockade of the impulses from atria to ventricle and appearance of spontaneous ventricular rhythm ($V_t$, beats/mis).

Measurements of glycolytic flux. To determine glycolytic flux a perfusion media containing 0.1 μCi/ml [D-3-$^3$H]glucose (15 Ci/mmol; American radiolabeled Chemicals Inc.) was perfused and after 15 min of equilibration in this medium, coronary venous effluents was continuously collected successively every 2 min throughout the duration of the experiment. At the end of the experiment the heart was removed, large vessels dissected out and placed in an oven to dry and thereafter weighed. Glycolytic flux was determined from analysis of $^3H_2O$ content in the venous effluent aliquotes since production of $^3H_2O$ during the enolase reaction of the Embden-Meyerhoff pathways is directly proportional to the flux in the glycolytic pathway To separate $^3H_2O$ from [$^3$H]glucose, 1 ml sample of perfusate was placed on a 1×4 cm column of Dowex-1 borate which retained labeled glucose. The column effluents was collected directly into counting vial and the column further washed with 2 ml of water. To these 3 ml of effluent scintillation liquid was added and counted. The rate of $^3H_2O$ release was determined as cpm/min per g dry weight and used to calculate glycolytic flux from the specific radioactivity of the perfused glucose. Glycolytic flux was expressed as μmol/min per g dry weight.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United State is:

1. An adenosine agonist or antagonist having a purine ring structure covalently coupled to a water-soluble dextran, wherein said dextran is covalently coupled to the 6- position or to the 8- position of said purine ring structure by reaction of cyanogen bromide activated dextran with the free amino group of a linker which is covalently bonded to said 6- position or 8- position and said linker is selected from the group consisting of $NH_2—(CH_2)_n—NH—$ where n=1-10, $NH_2—C_{6-20}$ arylene-, $NH_2—C_{5-6}$ cycloalkylene-, $—NH—C_6H_5—CH_2CONH—C_6H_5—CH_2CONH$ $—(CH_2)_n—NH_2$, $—C_6H_5—NH_2$, $—CH(NH_2)CH_2NH_2$ and $—C_6H_5—O$ $—CH_2—CONH(CH_2)_qNH$ $—(COCH_2—C_6H_5—)_r—NH_2$ where q=1-6 and r=0-1.

2. The covalently coupled adenosine agonist or antagonist of claim 1, wherein said dextran has a molecular weight of 1 kD-5000 kD molecular weight.

3. The covalently coupled adenosine agonist or antagonist of claim 1, wherein said dextran has a molecular weight of 1,000-2,000 kD.

4. The covalently coupled adenosine agonist or antagonist of claim 1, wherein said dextran has a molecular weight of 1-10 kD.

5. The covalently coupled adenosine agonist of claim 1, wherein said adenosine agonist or antagonist is adenosine.

6. The covalently coupled adenosine agonist or antagonist of claim 1, wherein said covalently coupled agonist or antagonist selectively binds adenosine $A_1$ receptors.

7. The covalently coupled adenosine agonist or antagonist of claim 1, wherein said covalently coupled agonist or antagonist selectively binds adenosine $A_2$ receptors.

8. The covalently coupled adenosine agonist or antagonist of claim 1, wherein said adenosine agonist or antagonist is an adenosine agonist.

9. The covalently coupled adenosine agonist or antagonist of claim 1, wherein said adenosine agonist or antagonist is an adenosine antagonist.

10. The covalently coupled adenosine agonist of claim 8, wherein said adenosine agonist has the structure shown below:

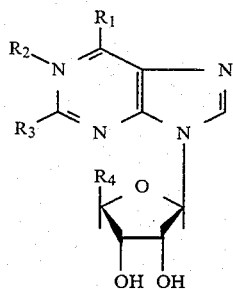

wherein $R_1$ is $NH_2-(CH_2)_n-NH-$, $NH_2-C_{6-20}$ arylene-, $NH_2-C_{5-6}$ cycloalkylene-, or $-NH-C_6H_5-CH_2CONH-C_6H_5-CONH-(CH_2)_n-NH_2$, where $n=1-10$; $R_2$ is hydrogen, halogen, or $C_{1-6}$ alkyl; $R_3$ is hydrogen, halogen, $C_{1-6}$ alkyl, or oxo and $R_4$ is hydroxymethyl, $C_{1-6}$ alkyl-carboximido or $C_{3-6}$ cycloalkyl-carboximido.

11. The covalently coupled adenosine agonist of claim 8, wherein said adenosine agonist is selected from the group consisting of $N^6$-phenyl-adenosine, $N^6$-$C_{5-8}$ cycloalkyl-adenosine, $N^6$-$C_{1-6}$ alkyl-adenosine-5'-uronamide, and 2-halo-adenosine.

12. The covalently coupled adenosine agonist of claim 8, wherein said adenosine agonist is selected from the group consisting of $N^6$-1-methyl-2-phenethyl-1-deazaadenosine, $N^6$-cyclopentyl-1-deazaadenosine, $N^6$-cyclohexyl-1-deazaadenosine, $N^6$-octylaminoadenosine, 2-(4-(2-carboxyethyl)phenethylamino)-5'-N-ethylcarboxylamidoadenosine, adenosine, $N^6$-(4-(2-aminoethylaminocarbonylmethylphenyl)adenosine, $N^6$-benzyladenosine, 2-chloroadenosine, 2-chloro-$N^6$-cyclopentyladenosine, $N^6$-cyclohexyl adenosine, $N^6$-cyclopentyladenosine, 5'-(N-cyclopropyl)-carboxamidoadenosine, 1-deaza-2-chloro-$N^6$-cyclopentyladenosine, 5'-N-ethylcarboxamidoadenosine, $N^6$-methyladenosine, $\alpha\beta$-methylene ATP lithium salt, 2-methylthio-ATP, 1-methylisoguanosine, 5'-N-methylcarboxamidoadenosine, $N^6$-phenyladenosine, $N^6$-phenylethyladenosine, 1-phenyl-2-isopropyladenosine, $N^6$-hydroxylphenylisopropyladenosine and $N^6$-azidophenylethyladenosine.

13. The covalently coupled adenosine antagonist of claim 9, wherein said adenosine antagonist is selected from the group consisting of adenosine, xanthine and theophylline.

14. The covalently coupled adenosine antagonist of claim 9, wherein said adenosine antagonist has the structure shown below

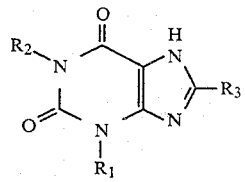

wherein $R_1$ is $C_{1-6}$ alkyl, $R_2$ is $C_{1-6}$ alkyl and $R_3$ is phenylamino, $-NH_2CHCH_2NH_2$, $-C_6H_5-O-CH_2-CONH(CH_2)_qNH$ $-(COCH_2-C_6H_5-)_r-NH_2$, where $q=1-6$ and $r$ is 0 or 1.

15. The covalently coupled adenosine antagonist of claim 8, wherein said adenosine antagonist is selected from the group consisting of aminophylline; 1-allyl-3,7-dimethyl-8phenylxanthine; theophylline ethylenediamine; 1-allyl-3,7-dimethyl-8-sulphoxanthine; 7-($\beta$-chloroethyl) theophylline; 4-amino-N-[2-[[4-(2,3,6,7-tetrahydro-2,6-dioxo-1,3-dipropyl-1H-purin-8-yl) phenoxy]acetyl]amino]ethyl benzeneacetamide; 8-[4-[[[(aminoethyl) amino]carbonyl]methyl]oxy]phenyl-1,3-dipropylxanthine; 8-cyclopentyl-1,3-dimethylxanthine; 8-cyclopentyl-1,3-dipropylxanthine; 1,3-diethyl-8phenylxanthine; 1,3-dimethylxanthine; 1,7-dimethylxanthine; 3,7-dimethylxanthine; 1,3-dipropyl-7-methylxanthine; 1,3-dipropyl-8-p-sulfophenylxanthine; 1,3-dipropyl-8-(2-amino-4-chlorophenyl)-xanthine: 3,7-dimethyl-1-propargyl xanthine; PACPX; 7-($\beta$-hydroxyethyl) theophylline; 3-isobutyl-1-methylxanthine; 8-[4-[[[2-(4-aminophenylacetylamino)ethylamino]carbonyl]methyl]oxy]phenyl-1,3-dipropylxanthine; 8-phenyltheophylline; 3-(n-propyl)-xanthine; 8-(p-sulfophenyl)-theophylline; and 8-[4-(2-aminoethylaminocarbonyl methoxy) phenyl]-1,3-dipropylxanthine.

16. A pharmaceutical composition comprising the covalently coupled adenosine agonist or antagonist of claim 1 and a pharmaceutically acceptable carrier or diluent.

* * * * *